US006963205B2

(12) United States Patent
Lundstrom et al.

(10) Patent No.: US 6,963,205 B2
(45) Date of Patent: Nov. 8, 2005

(54) ELECTRICALLY MEASURING SOIL DRY DENSITY

(76) Inventors: John W. Lundstrom, 1712 Earhart Ct., La Verne, CA (US) 91750-0369; Dennis Anderson, P.O. Box 1676, Carson City, NV (US) 89702; Dave Straley, P.O. Box 5406, Incline Village, NV (US) 89452; William Ehni, P.O. Box 4228, Carson City, NV (US) 89702; Darrell R. Word, P.O. Box 786, Leander, TX (US) 78646

( * ) Notice: Subject to any disclaimer, the term of this patent is extended or adjusted under 35 U.S.C. 154(b) by 0 days.

(21) Appl. No.: 10/644,393

(22) Filed: Aug. 18, 2003

(65) Prior Publication Data

US 2004/0095154 A1   May 20, 2004

Related U.S. Application Data

(60) Provisional application No. 60/404,900, filed on Aug. 21, 2002.

(51) Int. Cl.[7] ............................................. G01R 27/26
(52) U.S. Cl. ........................ 324/664; 324/663; 324/694
(58) Field of Search ................................ 324/694, 664, 324/663, 693, 324, 341, 344, 354, 358, 649, 324/654, 686, 689; 73/54.03, 61.71, 73–77; 702/50, 57, 100–101

(56) References Cited

U.S. PATENT DOCUMENTS

| | | | |
|---|---|---|---|
| 3,400,331 A | 9/1968 | Harris | |
| 3,671,857 A | 6/1972 | Bergmanis et al. | |
| 3,694,742 A | 9/1972 | Bergmanis et al. | |
| 3,769,581 A * | 10/1973 | Pullman | 324/694 |
| 3,781,672 A | 12/1973 | Maltby et al. | |
| 3,784,905 A | 1/1974 | Blackwol et al. | |
| 3,882,381 A | 5/1975 | Gregory | |
| 3,882,383 A * | 5/1975 | Matlin | 324/696 |
| 3,967,912 A | 7/1976 | Parker | |
| 3,992,665 A * | 11/1976 | Preikschat | 324/666 |
| 4,099,118 A | 7/1978 | Franklin et al. | |
| 4,389,136 A | 6/1983 | Fehrenbach | |
| 4,433,286 A | 2/1984 | Capots et al. | |
| 4,468,610 A | 8/1984 | Hanson | |
| 4,604,612 A | 8/1986 | Watkins et al. | |
| 4,766,369 A | 8/1988 | Weinstein | |
| 4,817,021 A | 3/1989 | Sowerby et al. | |
| 4,933,853 A | 6/1990 | Musil et al. | |
| 4,972,154 A | 11/1990 | Bechtel et al. | |
| 5,051,026 A | 9/1991 | Sovik | |

(Continued)

OTHER PUBLICATIONS

Anderson et al. U.S. Appl. No. 60/404/900 Aug. 21, 2002.

(Continued)

*Primary Examiner*—Anjan Deb
*Assistant Examiner*—M. Kramskaya

(57) ABSTRACT

The object of the Electrical Density Gauge (EDG) invention is to provide a low cost, portable, non-nuclear, and rugged field-use device that measures dry density in soils that have been constructed for use as road-beds and building foundations. This data is used to ensure the quality control of the constructed foundation. The electrical properties of soil are measured at a radio frequency using probes driven into the soil. To calibrate EDG, certain algorithms of these electrical properties are related to physically measured wet densities and unit weights of water for a plurality of calibration test spots. Correlation regressions are found, that are used to convert values of the electrical properties measured at unknown field test spots into values of dry density.

2 Claims, 3 Drawing Sheets

U.S. PATENT DOCUMENTS

| | | |
|---|---|---|
| 5,088,854 A | 2/1992 | Sovik |
| 5,134,380 A | 7/1992 | Jonas |
| 5,138,268 A | 8/1992 | Mulkey et al. |
| 5,210,500 A | 5/1993 | Pingel et al. |
| 5,213,442 A | 5/1993 | Sovik |
| 5,223,796 A | 6/1993 | Waldman et al. |
| 5,309,110 A | 5/1994 | O'Neill et al. |
| 5,363,051 A | 11/1994 | Jenstrom et al. |
| 5,378,994 A | 1/1995 | Novak et al. |
| 5,398,547 A | 3/1995 | Gerardi et al. |
| 5,436,565 A | 7/1995 | Gammell |
| 5,479,104 A * | 12/1995 | Cambell ............... 324/690 |
| 5,484,226 A | 1/1996 | Emerson et al. |
| 5,521,515 A | 5/1996 | Campbell |
| 5,551,288 A | 9/1996 | Geraldi et al. |
| 5,602,486 A | 2/1997 | Novak |
| 5,801,537 A | 9/1998 | Siddiqui et al. |
| 5,841,282 A * | 11/1998 | Christy et al. ............ 324/347 |
| 5,900,736 A | 5/1999 | Sovik et al. |
| 5,933,015 A | 8/1999 | Siddiqui et al. |
| 6,215,317 B1 | 4/2001 | Siddiqui et al. |
| 6,380,745 B1 * | 4/2002 | Anderson et al. .......... 324/347 |

OTHER PUBLICATIONS

Anderson et al. Disclosure Document Nr. 49,002 Mar. 26, 2001.

* cited by examiner

ELECTRICALLY MEASURING SOIL DRY DENSITY

RELATED PATENT DOCUMENTATION

This application is claims priority date of Aug. 21, 2002 and is the Utility Patent Application being made that related to Provisional Patent Application No. 60/404,900 that is titled Electrically Measuring Soil Density and Soil Moisture Content.

This application is also related to U.S. Disclosure Document titled Electrical Density Gauge, which was filed on Mar. 20, 2001 and recorded at the U. S. Patent and Trademarks Office as Disclosure Document No. 491002 on Mar. 26, 2001.

FIELD OF THE INVENTION

The invention relates to the field of measuring soil density for road and foundation construction. More particularly, the invention relates to the determination of soil density by means of electrical measurements of soil dielectric parameters. The measurement of electrical parameters as they relate to soil density and moisture content is useful in providing rapid, low cost, and efficient information about road and foundation soil as it is being compacted. The invention is termed "EDG", representing Electrical Density Gauge.

BACKGROUND OF THE INVENTION

Soil engineering and principles of soil mechanics have been used for centuries by builders and constructors to enable the construction of well-founded building and structures. Ancient civilizations throughout the world constructed palaces, temples, pyramids, aqueducts and roads that employed foundation preparation and excavations to establish solid footings. Since the beginning of recorded history mankind has known that to build a lasting structure, one must build on a solid foundation.

In 1773 a French physicist named Charles-Augustion de Coulomb published his theories on soil mechanics. He studied the properties of soil use for planning foundations for buildings and highways. A Scottish engineer named William Tankine in 1857 studied how soils react under stress and while being moved during construction. Since these early researches investigated soil-engineering properties, a wealth of knowledge has been amassed to help present day soil engineers safely design foundations and footing for civil construction and building. Standardized testing procedures have been developed to ensure public safety and uniformity in building practices. Most of the test procedures involve physical measurements and testing procedures to assess soil strengths and reactions to imposed loads by constructed structures.

The American Society for Testing and Materials (ASTM) was established in 1898 and has grown to one of the largest voluntary standards development systems in the world. Today ASTM standards are used by thousands of individuals, companies, and agencies. Scientists and engineers use them in their laboratories, architects and design engineers use them in their plans and government agencies reference ASTM standards in codes, regulations, and laws. The ASTM has 132 standards-writing committees. The committee that primarily deals with geotechnical engineering is the Committee D-18 on Soil and Rock. ASTM standards procedures are used and integrated with newly developed soil electrical measuring techniques to enable fast, accurate, and efficient determination of soil properties for civil engineering applications.

Knowing soil density and moisture content is of major importance in the construction of roads and foundations. Proper density and moisture are necessary to prevent premature failure of these constructions. To enable the construction of engineered foundations to meet civil construction specifications soils engineers must conduct geotechnical investigations to determine the character of the soil materials that will be used in the design and construction of the foundations. To properly engineer and design a foundation, the soil characterization is done by both laboratory and field tests that provide strength data that is used in the design calculations for that subject foundation. The routine laboratory test of evaluation of a soil material density is known as the proctor test. The ASTM D-698-00a "Standard Test Methods for Laboratory Compaction Characteristics of Soil Using Standard Effort (12,400 ft=lbs/ft$^3$ (600 kN/m$^3$))" or ASTM D-1557-00 "Standard Test Methods for Laboratory Compaction Characteristics of Soil Using Modified Effort (56,000 ft=lbs/ft$^3$ (2,700 kN/m$^3$))" are used to determine a soil materials maximum density at an optimum moisture content. Based on the type of foundation that is being designed, a civil engineer can write an engineering specification for the amount of compactive effort that must be applied to the soil to ensure a solid foundation for the given structure. The engineering soil specification will require that the foundation is built and tested to meet some design density criterion at a design moisture content. Field soil density measurements are made physically by a process involving a replacement of a known weight of soil with a measured amount of sand of known and repeatable density. This test is commonly known as the Sand Cone Test. ASTM D-1556-00 "Standard Test Method for Density and Unit Weight of Soil in Place by Sand Cone Method" provides a detailed procedure and protocol of conducting the test. Soil moisture content is measured by determining the weight loss after oven drying. ASTM has several test procedures for determining the moisture content of soil. ASTM D-2216-98 "Standard Test Methods for Laboratory Determination of Water (Moisture) Content of Soil and Rock by Mass"; ASTM 4643-00 "Standard Test Methods for Laboratory Determination of Water (Moisture) Content of Soil by Microwave Oven Heating"; and ASTM 4959-00 "Standard Test Methods for Laboratory Determination of Water (Moisture) Content of Soil by Direct Heating" are three of the geotechnical industry standards of measuring soil moisture.

In the sand cone test, an amount of compacted soil under test is removed from the construction site, weighed, and the moisture content determined. The hole from which the soil was removed is filled in a prescribed manner with sand of known density. The volume required to fill the hole is measured. The results of these measurements are used to determine the Wet Density, the Moisture Content, and the Dry Density of the soil. These are some of the engineering parameters necessary to determine that the soil construction is adequate for the intended use.

To permit more rapid field measurements of the physical character of the soil, the Nuclear Density Gauge is commonly used in conjunction with the sand cone test. The nuclear density gauge ASTM standard is 2922-96 "Standard Test Method for Density and Soil-Aggregate in Place by Nuclear Method (Shallow Depth)". The sand cone test is used to standardize the nuclear gauge for a specific type of soil, which allows the nuclear gauge to be used repeatedly in the same area on the same type of soil. This permits many more measurements on each site to be made quickly and without continual resort to the cumbersome sand cone test. Nuclear gauges are quite expensive and very costly to have repaired due to the nuclear source they contain. The nuclear density gauge suffers from some degradation of accuracy as a result of not taking care when using it, inclusion of rocks in the measured area, and because the nuclear source changes as a function of radioactive decay. Calibration of the nuclear gauge is costly and required frequently. And, handling of the nuclear gauge is subject to many rules and regulations imposed for the safety of the operators and the general public. Consequently, the nuclear gauge is costly to maintain, and difficult to manage.

One such micro-wave device is described as a density and moisture content measuring invention. (U.S. Pat. Nos. 5,801,537, 5,933,015, and 6,215,317—"Method and apparatus for measuring in-place soil density and moisture content", all to Siddiqui, et al.). The specifications describe how the volumetric moisture content can be estimated from measurement of the dielectric constant of a test sample of soil. It also infers that gravimetric density can be estimated from the same measurement of dielectric constant, by reference to another laboratory measurement. It is questionable that specific gravity can be measured using dielectric constant only, since in practice, two samples of soil can be prepared that have exactly the same dielectric constant, but have different gravimetric densities and gravimetric moisture contents.

Laboratory testing during the invention of EDG showed that a much higher correlation to the unit weight of water in a soil sample can be achieved using the quotient off measured volume capacitance and measured volume resistance, which is a new and novel feature of the EDG invention.

SUMMARY OF THE INVENTION

The objects of the invention are to provide a low cost, stable, portable non-nuclear, and rugged field-use device that measures wet density, and dry density in construction materials soils that have been constructed for use as road beds and building foundations.

Principals of soil mechanics are important to understand the relationship of physical soil properties to measured electrical properties. Soil mechanics relates to the study of the response of masses composed of soil, water and air to imposed loads. By employing principals of soil mechanics which provides the analytical tools required for foundation engineering, retaining wall design, highway and railway subbase design, tunneling, earth dam design, mine excavations design engineers are able to design civil structures with appropriate factors of safety for public use. Soil consists of a multiphase aggregation of solid particles, water and air. This fundamental composition gives rise to unique engineering properties as evaluated with both physical characteristics measurements and electrical measurements. The description of the mechanical behavior of soil requires some of the most sophisticated principles of engineering mechanics. The present invention integrates the complex science of soil mechanics with electrical engineering to provide efficient evaluation of soil materials that are used in civil construction.

The Electrical Density Gauge (EDG) invention provides maintenance free, and rapid measurement of the electrical dielectric properties of soil that can be related to soil wet density, and dry density. Because soils have such a wide variety of characteristics that affect the electrical dielectric properties, it is necessary to employ the sand cone test as a calibration means for the various specific types of soils. The frequency of the sand cone tests required for good accuracy and correlation is the same as that already practiced when using the nuclear density gauge.

The EDG provides advantages over the nuclear gauge and other radio frequency means, because it is low cost, light and portable, battery powered, and not subject to calibration degradation over time. Once standardized against a sand cone test, the EDG will provide results that are as good as, or better than the nuclear gauge. Results are computed and displayed immediately, and stored for download at a later date.

The measurement circuit of the EDG contains a 3 mHz. radio frequency source that is applied to the soil under test by spike type probe electrodes that are pushed into the soil to a prescribed depth and distance apart. The volume of soil that is measured is controlled by the depth and spacing of the measurement probes. The radio frequency current that is passing through the probes into the soil and the voltage that appears across the probes are measured electronically. Additionally the electrical phase relationship between the soil current and the probe-to-probe voltage is determined. These parameters are termed Is for soil current, Vs for probe-to-probe voltage, and Ps for their phase relationship.

FIG. 1 shows the simplified measuring circuit and identifies the measured parameters. Rcs is the current sensing resistor across which a voltage is measured to enable the determination of soil current.

The electrical dielectric parameters of the soil are then calculated using well known electrical engineering equations that use Is, Vs, and Ps to determine the equivalent values of soil Resistance (Rs) and soil Capacitance (Cs).

Calibration of the EDG invention for a specific soil type involves first taking a series of electrical measurements in a chosen spot of the site under test. These measurements are then stored. A geotechnical (sand cone) test is then performed on the center of the spot where the electrical measurements were taken. This assures that the soil that is used for physical measurements is the same for which electrical values were taken.

When calibrating the EDG for a specific soil type, two equations are generated that relate the soil physical properties to the calculated electrical dielectric parameters. First an equation is derived that represents the relationship between soil wet density and soil electrical real impedance. Then a second equation is derived that relates the soil unit weight of water to the quotient Cs/Rs. It has been found through considerable testing of various soil types and calculations with synthetic modeled soil physical parameters, that these relationships provide a good prediction of the soil physical properties using the equivalent electrical parameters calculated from measured electrical dielectric properties. In practice, linear regression equations are used to relate the measured electrical parameters to the measured physical parameters. Over a wide range of density and moisture it may be desirable to employ non-linear equations for better accuracy.

After calibration for a specific soil type, the equivalent electrical values (Rs, Cs) of the soil under test are computed, then used to calculate the Real Impedance and the Cs/Rs quotient. These values are then applied to the soil specific equations generated during calibration. The resulting values of wet density and unit weight of water are then used to calculate soil dry density using equations that are well known by geotechnical engineers.

Measurements of the soil electrical parameters (Is, Vs, Ps) are made with circuitry that is well known in the field of electronic engineering, and implementation of these measurement means can take a variety of forms. The frequency source used in the EDG operates at 3.0 mHz. The EDG invention is capable of making the described measurements at other radio frequencies without any change to the substance of the invention.

The EDG uses a micro-processor based mini-computer module that contains memory, processing, A/D converters, keypad entry, RS-232 I/O ports, LCD display, and other features that are useful in the computation and handling of electrical signals. This computer utilizes proprietary programming to convert the electrical signals Is, Vs, and Ps to representative digital form, then the computes actual soil electrical values measured each time the soil is tested. The type and configuration of the computer is not specific to the EDG with the exception that it must have the requisite resources to enable the necessary calculations and input-output resources.

From the electricalsoil measurements, the software then calculates Rs and Cs, the quotient Cs/Rs, and real impedance (Zs). Cs/Rs is then applied to the equation that was generated when the EDG was calibrated on soil for which the physical parameters were determined by the sand cone test. The result is the unit weight of water in the soil under test. Zs is applied to its respective equation resulting in the wet density of the soil under test. These measured physical parameters are used to determine dry density. These final values are displayed on the computer display and stored for future download as required.

The soils engineers expect also to see the percent of maximum compaction that the measured dry density would provide. This additional output requires another physical test on the soil that is typically performed under ASTM D-698-00a "Standard Test Methods for Laboratory Compaction Characteristics of Soil Using Standard Effort (12,400 ft=lbs/ft$^3$ (600 kN/m$^3$))" or ASTM D-1557-00 "Standard Test Methods for Laboratory Compaction Characteristics of Soil Using Modified Effort (56,000 ft=lbs/ft$^3$ (2,700 kN/m$^3$))." The procedure specifies that a several kilogram sample be prepared at increasing moisture contents and then the various prepared samples are compacted in a standard proctor mold using a specified compactive effort. The test results in determining a value of maximum compaction and optimum moisture content for the soil that is being tested. The EDG will accept the results of this test as an input, calculate, and display the percent of maximum compaction that results from the estimated value of dry density.

Geotechnical and soils engineers will find that the EDG invention has practical use in conjunction with the sand cone test, and that the nuclear gauges can be replaced. The following more detailed description of the preferred embodiment of the EDG invention will make its advantages more apparent.

DETAILED DESCRIPTION OF THE PREFERRED EMBODIMENT

Figure 1:
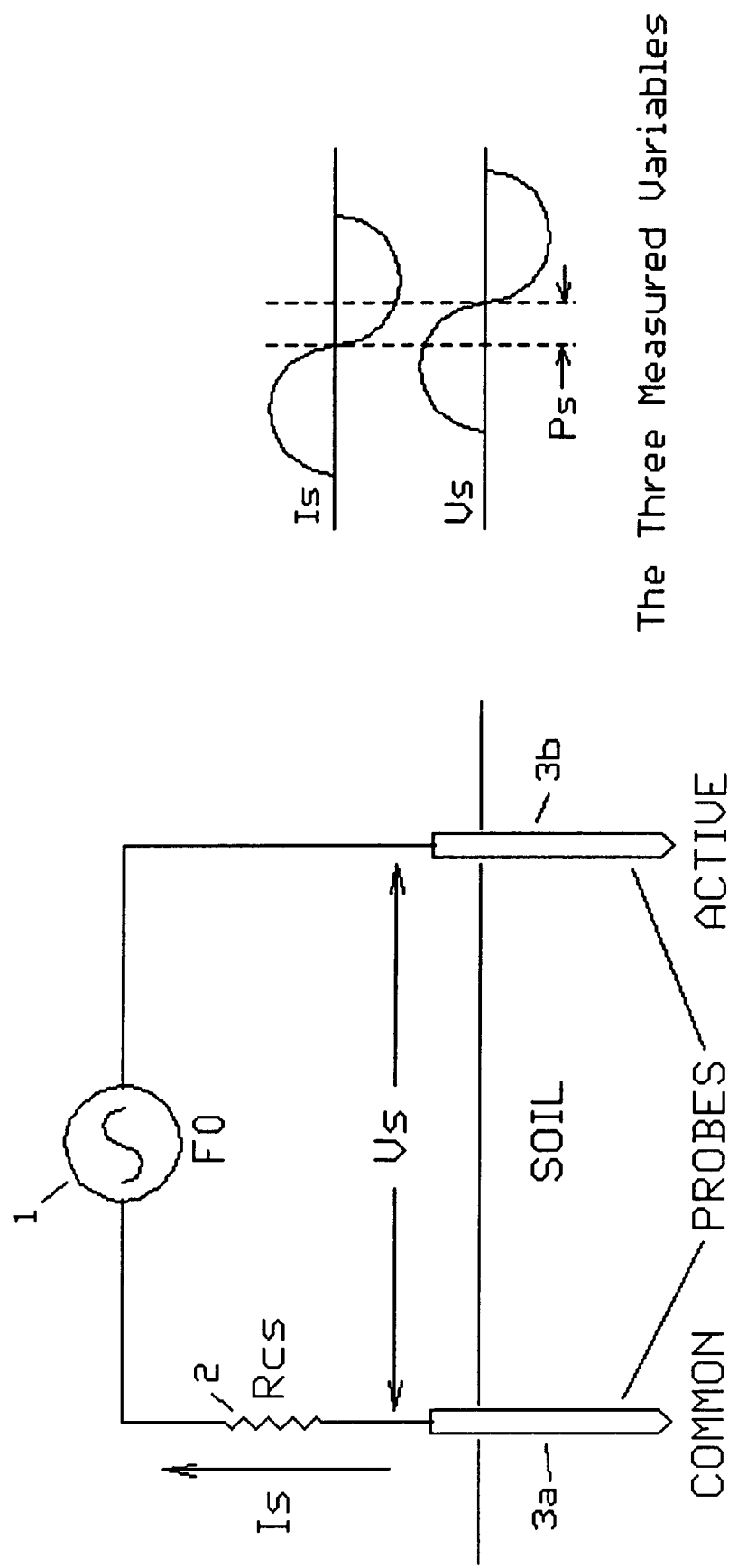
FIG. 1 shows the simplified measurement circuit of the EDG as relates to soil electrical measurements.
Figure 2:
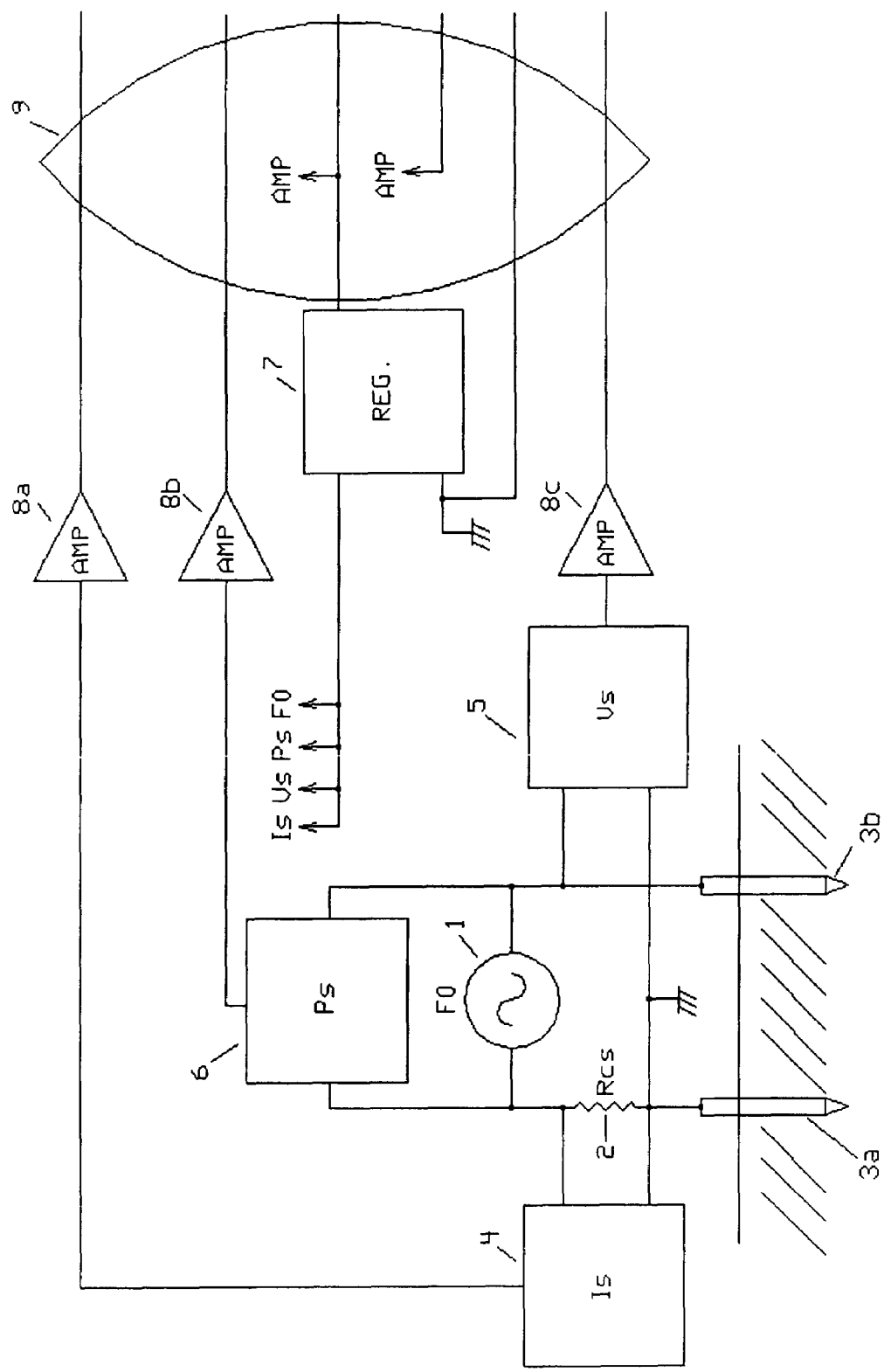
FIG. 2 shows the block diagram of the various circuit blocks that comprise the EDG measuring circuitry.
Figure 3:
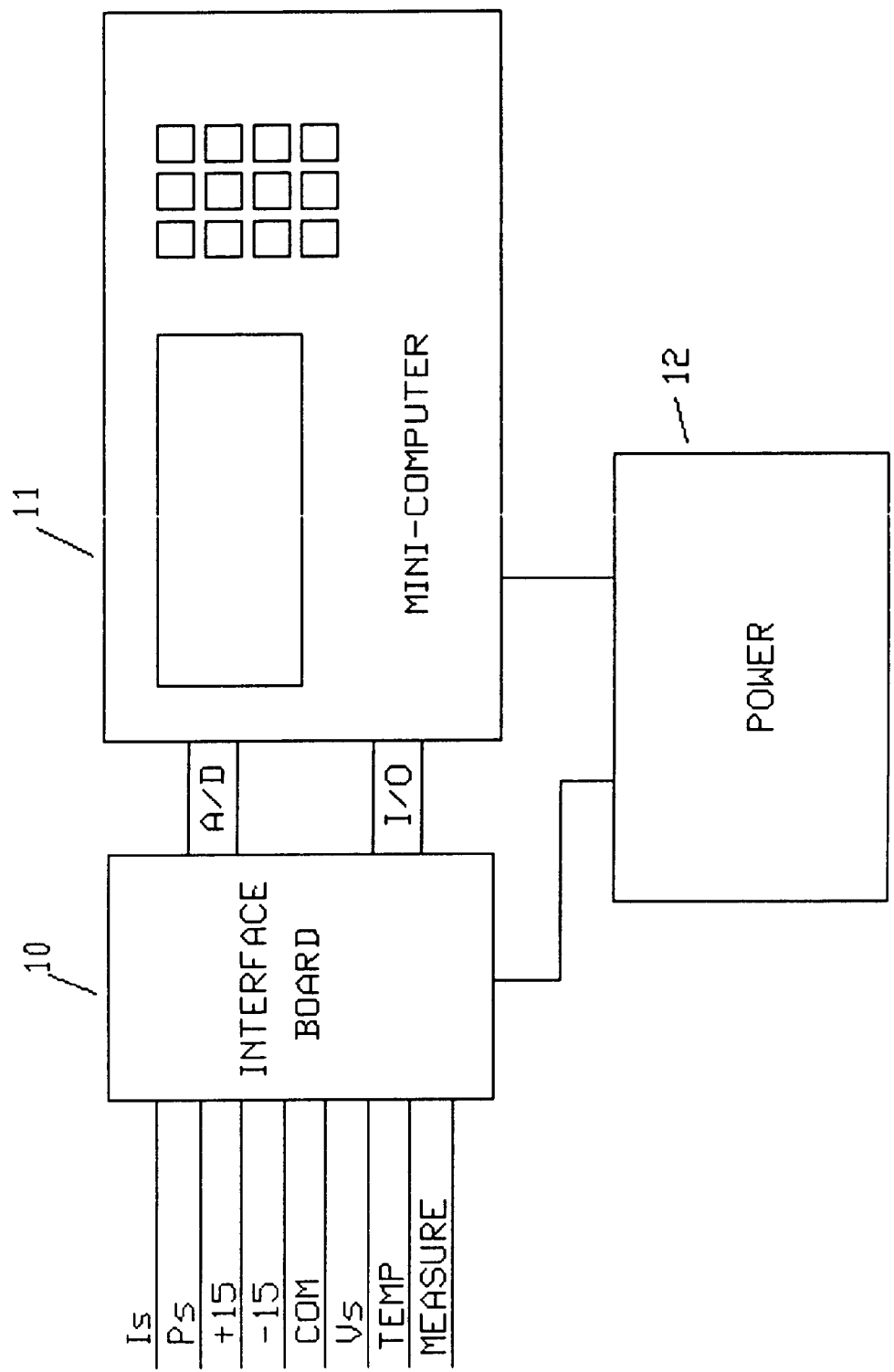
FIG. 3 shows the block diagram of the EDG console electronics.

An embodiment of the EDG invention is described with reference to the figures using reference designations as shown in the figures. Referring to FIG. 2, the measurement components of the preferred EDG invention comprise a 3.0 mHz sinusoidal voltage source (Fo) 1, a current sensing resistor (Rcs) 2, soil electrode probes 3$a,b$, a voltage measurement circuit that measures the voltage across the current sensing resistor 4, a voltage measurement circuit that measures the voltage across the two soil electrical probes 5, a phase difference measurement circuit that determines the phase difference between the current related voltage and the soil related voltage 6, local power regulators 7, and buffer amplifiers 8 that send the measured signals through a cable 9 to the EDG Console interface circuit board 10 (FIG. 3)

The soil electrical probes 3$a,b$ are 3 in.×¼ in. dia. steel rod that has been tapered for easier entry into the soil. Alternately, conical or other configuration soil electrical probes are equally suitable for assuring ease of penetration and good contact with the soil. The soil electrical probes are typically spaced from 3 in. to 12 in. apart when measuring roadbed or foundation soil constructions. Some dry soils are so hard when compacted that it is necessary to hammer hardened steel rods in, to enable electrode penetration. In this case the EDG electrode probes will be made to touch the hardened rods to achieve an electrical connection when the measurement is made. Alternately, short cables with spring clips can be used to make connection between the EDG probes and the hardened rods. Electrical probe dimensions and spacing can be varied as required by the volume of soil required to be measured.

The sinusoidal voltage source 1 comprises a single transistor Hartley oscillator with a toroidal tank circuit inductor. The output voltage to the measurement circuitry is taken from a second winding on the toroid that results in a low impedance output to the measurement circuit. Other oscillator types can be used in the EDG invention with equally successful results.

The current sensing resistor (Rcs) 2 is a 1,000 Ohm 1% resistor. This value is chosen to optimize the measured resistance results as relates to the measurement volume of electrical probes and may vary depending upon the probe configuration.

The voltage measurement circuits 4, 5 are synchronous detectors that develop a DC output voltage that is proportional to the peak voltage of the RF sinusoidal AC wave being measured. Other RF sinusoidal AC wave measurement circuits can be configured to accomplish the same task as those used in this preferred embodiment.

The phase difference measurement circuit 6 is based upon a phase locked loop IC, where EDG is using the phase comparator part of the available circuitry. Other phase difference measurement circuits can be designed, that will accomplish the same task as what is described in this preferred embodiment.

The buffer amplifiers 8$a,b,c$ are typical frequency compensated IC op-amp chips and provide such gain and offset as is required to enable the correct processing of the specific range of voltage that is handled by the respective amplifier. Values of gain and offset may change as relates to the probe configuration.

The voltage regulator 7 is a 5 VDC three terminal IC regulator. Local regulation is provided for best stability.

Other voltages than 5 VDC can be used to power circuitry that accomplishes the same tasks as described in this preferred embodiment.

Cable 9 connects the local measurement circuitry to the EDG Console and Display unit. This cable is typically 6 ft. long and is of multi-conductor jacketed construction. The cable is connected to the EDG Console through a multi-pin removable connector. The EDG Console has a mating connector that is connected with internal wiring to the interface circuit board 10. This interface board contains a power supply that generates a source of positive and negative voltage used by the local measurement circuitry as well as other components on the interface board. This power supply is powered by the system storage battery. Additionally, the interface board contains an electronic switch that switches the voltages to be measured for use by the two A/D converters found in the mini-computer 11. The electronic switch is driven from I/O ports in said computer.

The mini-computer is a micro-controller based small general purpose computer that contains display, memory, serial I/O, digital I/O, and A/D converters, to name some of the main features of this unit.

Lastly, a rechargeable storage battery 12 provides power to the EDG system components as required. A panel switch is used to turn the EDG on or off.

What is claimed is:

1. An Electrical Density Gauge consisting of electrode means for electrically connecting to an in-situ test spot of compacted construction material (soil), electrical means for measuring the equivalent parallel resistance and equivalent parallel capacitance of said material, and means for performing the necessary computations and display of results, is calibrated by first measuring a plurality of in-situ test spots in a field of said construction material to determine values of said equivalent resistance and capacitance, then determining with the use of geotechnical means, the in-situ wet density and in-situ weight of water of the same plurality of test spots where electrical measurements were made, and with the use of said electronic computational means, the real impedance of the measured test samples is determined, the best fit regression equation between the physical wet density data points and real impedance data points is calculated, and also with the use of said electronic computational means, the ratio of measured capacitance and measured resistance is determined for all data points, then the best fit regression equation between the unit weight of water data points and capacitance/resistance ratio data points is calculated, said Electrical Density Gauge after being thus calibrated, is used to measure field test spots of the same type of construction material with previously unknown electrical characteristics and with the newly determined values of real impedance and capacitance/resistance ratio applied to the aforementioned regression equations, to compute a value of wet density and a value of unit weight of water for said unknown test spot, and using the aforementioned electronic computational means, the dry density of the constructional material at the unknown test spot is calculated from the wet density and unit weight of water.

2. The Electrical Density Gauge of claim 1, wherein the value of maximum dry density of the tested constructional material as determined by geotechnical means is entered into the aforementioned computational means, and used with the newly determined value of dry density to compute the percent of maximum compaction of the constructional material at each field test spot.

* * * * *